US010143969B2

(12) United States Patent
Acciarri et al.

(10) Patent No.: US 10,143,969 B2
(45) Date of Patent: Dec. 4, 2018

(54) COMPOUNDS FOR THE CAPTURE OF CARBON DIOXIDE FROM GASEOUS MIXTURES AND SUBSEQUENT RELEASE, RELATED PROCESS AND PLANT

(71) Applicant: UNIVERSITA DEGLI STUDI DI MILANO-BICOCCA, Milan (IT)

(72) Inventors: Maurizio Filippo Acciarri, Milan (IT); Simona Olga Binetti, Milan (IT); Bruno Vodopivec, Arcore (IT); Maurilio Giuseppe Meschia, Asti (IT)

(73) Assignee: UNIVERSITA DEGLI STUDI DI MILANO-BICOCCA, Milan (IT)

( * ) Notice: Subject to any disclaimer, the term of this patent is extended or adjusted under 35 U.S.C. 154(b) by 0 days.

(21) Appl. No.: 15/111,649

(22) PCT Filed: Jan. 16, 2015

(86) PCT No.: PCT/IB2015/000038
§ 371 (c)(1),
(2) Date: Jul. 14, 2016

(87) PCT Pub. No.: WO2015/107416
PCT Pub. Date: Jul. 23, 2015

(65) Prior Publication Data
US 2016/0346734 A1    Dec. 1, 2016

(30) Foreign Application Priority Data
Jan. 16, 2014  (IT) .............................. MI2014A0048

(51) Int. Cl.
B01D 53/14    (2006.01)
B01D 53/18    (2006.01)
(Continued)

(52) U.S. Cl.
CPC ......... *B01D 53/96* (2013.01); *B01D 53/1425* (2013.01); *B01D 53/1475* (2013.01);
(Continued)

(58) Field of Classification Search
CPC ........ Y02C 10/04; Y02C 10/06; B01D 53/62; B01D 53/1425; B01D 53/1475;
(Continued)

(56) References Cited

U.S. PATENT DOCUMENTS

| 2,649,166 | A | * | 8/1953 | Eck | ........................ | B01D 53/62 |
| | | | | | | 95/166 |
| 3,744,566 | A | * | 7/1973 | Szabo | .................... | C09K 8/588 |
| | | | | | | 166/275 |

(Continued)

FOREIGN PATENT DOCUMENTS

| EP | 0 000 224 | 1/1979 |
| EP | 0 214 898 | 3/1987 |

OTHER PUBLICATIONS

Buhler et al. "Ionic reactions and pyrolysis of glycerol as competing reaction pathways in near- and supercritical water" Journal of Supercritical Fluids 22 (2002) 37-53 (Year: 2002).*

(Continued)

*Primary Examiner* — Amber R Orlando
*Assistant Examiner* — Syed T Iqbal
(74) *Attorney, Agent, or Firm* — Wenderoth, Lind & Ponack, L.L.P.

(57) ABSTRACT

The present invention relates to novel molecules suitable to the use in the separation/removal of carbon dioxide from gaseous mixtures as liquid-phase carbon dioxide absorbers and suitable to allow the subsequent release of the absorbed carbon dioxide in form of different ionic liquids, preferentially a glycine salt with choline hexanoate, ester between glycine and hexanoic alcohol (hexyl glycinate) and glycerol (Continued)

ester with glycine and hexanoic acid. The present invention also relates to a method and a plant for the capture of carbon dioxide from gaseous mixtures by using an absorber for carbon dioxide in liquid phase with a heating jacket.

19 Claims, 5 Drawing Sheets

(51) Int. Cl.
*C07C 229/08* (2006.01)
*B01D 53/96* (2006.01)
*B01D 53/62* (2006.01)
*B01D 53/78* (2006.01)

(52) U.S. Cl.
CPC ......... *B01D 53/1493* (2013.01); *B01D 53/18* (2013.01); *B01D 53/62* (2013.01); *B01D 53/78* (2013.01); *C07C 229/08* (2013.01); *B01D 2252/2053* (2013.01); *B01D 2252/20421* (2013.01); *B01D 2252/20463* (2013.01); *B01D 2252/30* (2013.01); *B01D 2257/504* (2013.01); *B01D 2258/0283* (2013.01); *Y02C 10/04* (2013.01); *Y02C 10/06* (2013.01)

(58) Field of Classification Search
CPC .... B01D 53/1493; B01D 53/18; B01D 53/78; B01D 53/96; B01D 2252/20421; B01D 2252/20463; B01D 2252/2053; B01D 2252/30; B01D 2257/504; B01D 2258/0283; C10K 1/16; C07C 229/08; Y02A 50/2342
See application file for complete search history.

(56) References Cited

U.S. PATENT DOCUMENTS

| 5,618,506 | A | * | 4/1997 | Suzuki | ............... | B01D 53/1475 |
|---|---|---|---|---|---|---|
| | | | | | | 423/226 |
| 2012/0204717 | A1 | | 8/2012 | Dinnage | | |

OTHER PUBLICATIONS

International Search Report dated Aug. 19, 2015 in corresponding International (PCT) Application No. PCT/IB2015/000038.
Gouveia et al., "Toxicity of ionic liquids prepared from biomaterials", Chemosphere, vol. 104, Nov. 21, 2013, pp. 51-56.

* cited by examiner

COMPOUNDS FOR THE CAPTURE OF CARBON DIOXIDE FROM GASEOUS MIXTURES AND SUBSEQUENT RELEASE, RELATED PROCESS AND PLANT

FIELD OF APPLICATION

In its more general aspect, the present invention relates to the removal of carbon dioxide from a gaseous mixture containing it.

In particular, the present invention relates to novel molecules suitable to the use in the separation/removal of carbon dioxide from gaseous mixtures as liquid-phase absorbers of carbon dioxide and suitable to allow the subsequent release of the absorbed carbon dioxide.

The present invention also relates to a method and a plant for the capture of carbon dioxide from gaseous mixtures by using a liquid-phase absorber for carbon dioxide.

BACKGROUND OF THE ART

As it is known, among the most important objects in the energy and environmental fields there are undoubtedly the reduction of the concentration of greenhouse gases in the atmosphere and the storage thereof. In this regard, of particular interest is the separation of carbon dioxide ($CO_2$) from gases introduced in the atmosphere, such as, for example, industrial fumes and combustion gases.

Furthermore, carbon dioxide is present in natural gas, biogas, and other gaseous mixtures of industrial use. In this case also, is carbon dioxide separation is required in order to improve the quality specifications of gas for industrial use.

Different technologies for separating $CO_2$ from a gaseous mixture are present in the commerce. The selection of the technology to be used depends on the purity required for the product, and on the conditions of the gas to be treated (temperature, pressure, impurities present or concentration of $CO_2$ in the gas).

However, the high costs and the energy required by the currently available processes which are based on such known technologies represent the main obstacles to the actual use thereof. Typical applications are the purification of industrial fumes, natural gas (methane) or biogas, while the direct capture of carbon dioxide from the atmosphere still remains a far target, due to the huge volumes of air to be treated (due to the low concentration of $CO_2$ in the air, below 400 ppm [http://co2now.org/]).

The most widespread types of purification plants for $CO_2$-rich gases are essentially attributable to techniques which use:
  gas-selective membranes,
  low-temperature methanol,
  water at variable pressure, or
  basic solutions of ammonia or amines, free or absorbed onto solid supports.

Each of these techniques has drawbacks, such as investment or maintenance cost, problems of environmental dispersion, use of high amounts of water, corrosion processes of the plant.

More in detail, as regards to the technology of $CO_2$ separation by using a gas-selective membrane, as described for example in U.S. Pat. No. 8,052,776, it shall be noted that such technology does not ensure, compared to the chemical absorption, a good quality of the extracted gas, and it requires a gas in inlet with a low partial pressure of $CO_2$. On the other hand, the use of membranes having a high efficiency, as described for example in U.S. Pat. No. 8,506,677, requires a high investment cost, in addition to multiple extraction steps to achieve an acceptable separation. Furthermore, the membranes can easily obstruct, due to the micro-particles dragged by the gas passing through such membranes. This requires frequent interruptions of the process for cleaning the pores, with additional operative costs.

A known technology, alternative to the use of gas-selective membranes, is based on chemical processes of liquid-phase carbon dioxide absorption, which mainly exploit the acid feature of carbon dioxide. The absorbent molecules can be some organic amines, as described for example in EP 2514509 and WO 2012142668, or alkali metal hydroxides, as described for example in U.S. Pat. No. 8,119,091. In the case of organic amines, the main problem relates to the environmental dispersion. Simple amines are typically volatile, with a medium-high toxicity. This necessarily leads to configure the plant so as to ensure a perfect confinement of the vapors. The reaction between carbon dioxide and amines leads to the formation of http://co2now.org, which, by providing heat, releases $CO_2$, thus regenerating the starting amine. The thermal energy necessary for the release is related to the molecular structure of the amines. For the simple amines, the temperature required for the decarboxylation reaction is near to the boiling temperature of the free molecule, and this complicates the problems of vapor confinement.

The alkali hydroxides are safer as regards the environmental dispersion, but they have a high basicity, resulting in corrosion problems. Therefore, the hydroxides have to be used in more or less diluted aqueous solutions, and this involves an excessive absorption of thermal energy in the releasing steps. The reaction product of carbon dioxide with an inorganic hydroxide is bicarbonate. Sodium bicarbonate, for example, has a solubility in water of about 100 g/L. Therefore, during the absorption step, the precipitation of bicarbonate micro-crystals inside the reactor is possible.

Recently, the ionic liquids for the continuous absorption of carbon dioxide have been introduced. These are liquid-phase organic salts, and some of them have a specific reactivity with carbon dioxide via the formation of carbamic acid or by a dipolar interaction. See, for example, the ionic liquids described in US 20120186993, U.S. Pat. No. 7,527,775 and WO 2012033991. The ionic liquids have been mainly used in the gas-selective membranes, as described for example in US 20130225401, in the form of a polymer, as described, for example, in WO 2006026064, or via electrospray devices, as described for example in U.S. Pat. No. 8,480,787. However, the known ionic liquids used for the capture of carbon dioxide are typically complex molecules, so that their synthesis turns out to be expensive, as well as their not very interesting use for an industrial application. Furthermore, many ionic liquids have high viscosities, which limit the efficiency thereof.

As the gas-selective membranes having amines as the absorbing molecules, also the ionic liquids can be cooled by promoting the release of $CO_2$ previously absorbed by carbamic acid. However, such process requires a considerable energy consumption. It follows that the stripping process requires the introduction of heat to promote the cleavage of the bond between the carbonyl carbon and the nitrogen of the carbamate. Inversely, in the absorption step, the carbamate formation reaction produces heat which, if it is not subtracted from the system by a suitable cooling system, reduces the efficiency of the reaction.

In this context, systems exploiting the combination of a basic organic molecule capable of absorbing $CO_2$ with an apolar solvent are also known. In fact, the presence of apolar molecules in admixture with some types of absorbing molecules promotes the release of carbon dioxide. This phenomenon is due to the change in the polarity of the absorber molecule bound to $CO_2$ with respect to the free state, i.e., the initial state in the original form not bound to $CO_2$. In particular, carbamate which is formed during the absorption step is more polar compared to the molecule in its initial state, i.e., with a free amine group. Therefore, the $CO_2$ releasing step is promoted if in the absorbent mixture there is an apolar solvent, also called anti-solvent, due to a higher affinity towards the apolar solvent of the low polarity molecule which is reforming. This phenomenon is known as polarity swing assisted process (PSAR), and it is disclosed also in U.S. patent 2013/0056676. However, such system provides for the use exactly of an apolar solvent (anti-solvent), which is a non-biodegradable hydrocarbon. Furthermore, the anti-solvent hardly has ideal characteristics of miscibility with the absorbent species, necessary to ensure a process of absorption efficient that is efficient and, at the same time, a low vapor pressure and a high self-ignition temperature, both of which are undesired conditions due to obvious environmental and plant safety reasons.

Therefore, it is the main object of the present invention to provide a method for the separation of carbon dioxide from a gaseous mixture by using an liquid-phase absorber which has a high efficiency and a low environmental impact, while having an easy and cost-effective production for an industrial application, so as to overcome the limits of the above-mentioned known technologies for capturing carbon dioxide.

Another object of the present invention is to provide a method for the release of carbon dioxide from the liquid-phase absorber used for the capture thereof, which has a high efficiency, a low environmental impact and which requires reduced operative temperatures.

Still a further object of the present invention is to provide a plant capable of optimizing the heat exchange between the absorption step and the releasing step so as to minimize the energy intake.

SUMMARY OF THE INVENTION

After extensive research, the inventors identified novel compounds suitable to the use as liquid-phase absorbers of carbon dioxide which allow brilliantly achieving the above-mentioned objects.

According to an embodiment of the invention, the novel compounds are ionic liquids having the following general formula (I) or (II)

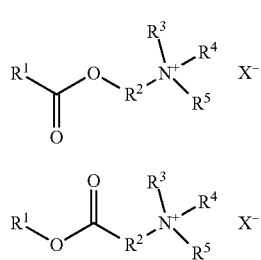

wherein R3, R4, R5 are each independently H, a C1-C6 alkyl group or an aromatic group, R2 is a C1-C6 alkyl group, R1 is a C5-C19 alkyl group, and $X^-$ is a carboxylate anion of a natural or artificial amino acid.

The term "ionic liquid" means in the present description a ionic compound having a melting point below 80° C., preferably below 50° C. at atmospheric pressure. The term "ionic liquid" does not exclude the presence or addition of other components or solvents to the ionic compound. In particular, the ionic liquid can include solvents such as water.

According to another embodiment of the invention, the novel compounds are glycerol esters having the general formula (III)

wherein the groups R6, R7 and R8 are selected from H, an acyl group of formula $R^9$—C(=OR)— where R9 is a C5-C19 alkyl group, an amino-acyl group deriving from a natural or artificial amino acid or an acyl residue of ectoin of formula (IV),

and wherein at least one of the groups R6, R7, R8 is an acyl group of formula $R^9$—C(=OR)— and at least one of the groups R6, R7, R8 is an amino-acyl group deriving from a natural or artificial amino acid or an acyl residue of ectoin of formula (IV).

According to a further embodiment, the novel compounds are esters, having the general formula (V)

wherein R10 is a C5-C19 alkyl group and R11 is an amino-acyl group deriving from a natural or artificial amino acid or an acyl residue of ectoin of formula (IV)

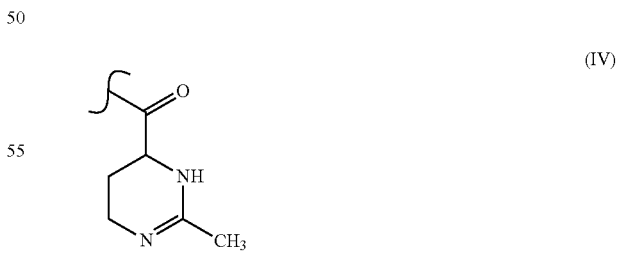

Each of the groups R1, R2, R3, R4, R5 R9 and R10 can be substituted or unsubstituted, and it can be cyclic, straight or branched chain optionally having at least one carbon-carbon double bond in the cis or trans configuration, and optionally having at least one carbon-carbon triple bond. When the alkyl group has more than a carbon-carbon double or triple bond, such bonds can be conjugated or non-conjugated. Each alkyl or aromatic group can be optionally substituted with one or more substituents, which can be the same or different.

Amino acids can be natural or artificial, as well as they can be amino acid analogs (for example, taurate). Such amino acids can be selected from, e.g., the natural 20 amino acids (alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine), and artificial amino acids, such as pyrrolysine and selenocysteine.

DETAILED DESCRIPTION

The synthesis of the ionic liquids according to the general formula (I) can provide for a first nucleophilic substitution reaction between a carboxylic acid (fatty acid with C5-C19 alkyl chain) and an halogenating agent to form an acyl halide, thus an esterification reaction between the hydroxyl group of choline and the carbonyl of acyl chloride. An ionic exchange between chloride and hydroxide ion and the salification with a natural or artificial amino acid then follow. An exemplary scheme illustrating the synthesis of glycine salified with choline hexyl-ester is set forth herein below:

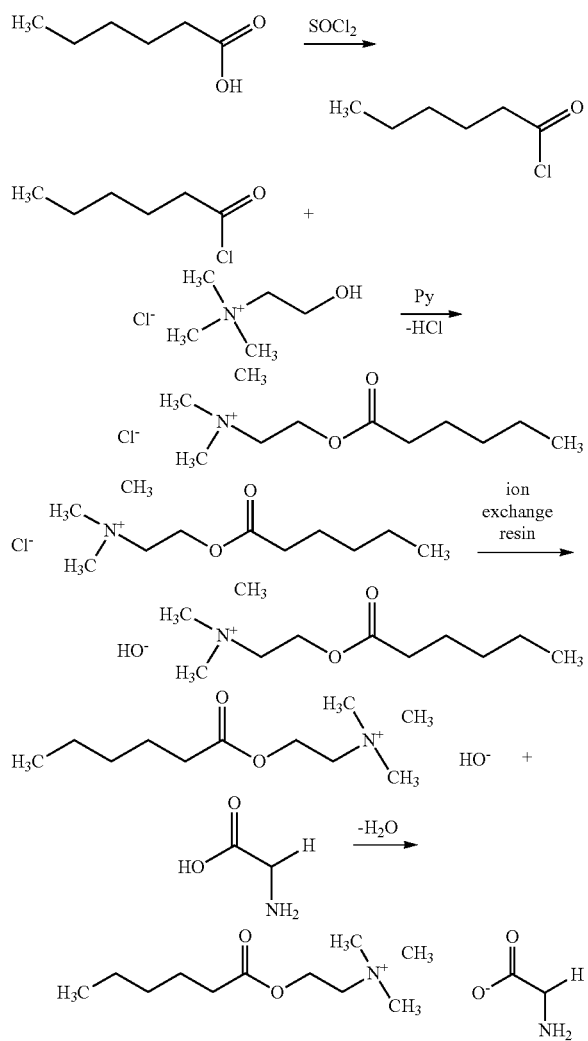

The synthesis of the ionic liquids according to the general formula (II) can provide for the deprotonation of an alcohol (fatty alcohol with C5-C19 alkyl chain) to form an alkoxide. An esterification reaction directly follows between the deprotonated hydroxyl group of the alkoxide and the carboxyl group of betaine. Finally, a salification with a natural or artificial amino acid occurs. An exemplifying scheme illustrating the synthesis of salified glycine with betaine trimethyl glycine hexyl ester is set forth below:

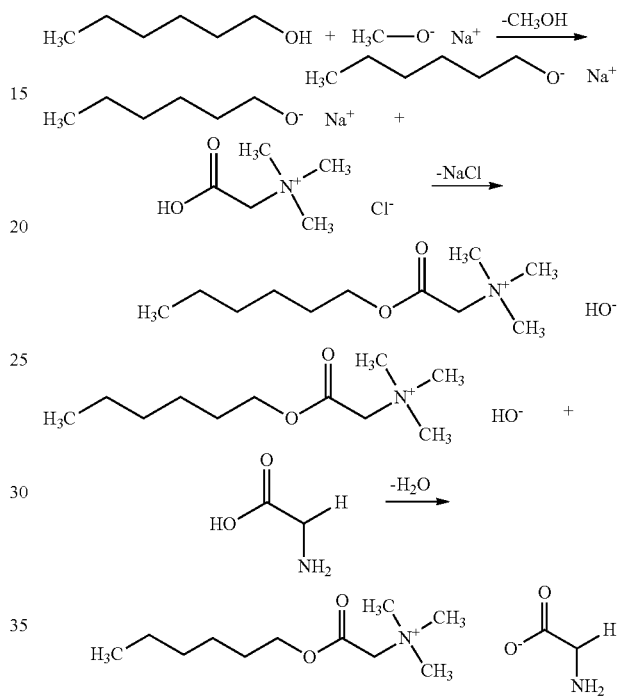

The synthesis of the esters of formula (V) formed between alcohol (fatty alcohol with C5-C19 alkyl chain) and natural or artificial amino acid or ectoin occurs by a simple esterification reaction, per se known in the art.

The synthesis of the esters of formula (III) formed between glycerol, carboxylic acids (fatty acids with C5-C19 alkyl chain) and amino acid or ectoin can be carried out by a simple basic catalysis, removing water by heating, for example, through a vacuum pump or preferably through molecular sieves.

It shall be noted that the novel compounds according to the present invention can be obtained from naturally occurring materials which are easily available, in particular from materials of vegetal origin naturally occurring in microalgae (for example, the fatty acids and the glycerol from oleic extract of the microalga and the amino acids from the protein panel after enzymatic hydrolysis) and which in turn can be obtained for example starting from simple microalgal cultures. At the same time, the novel compounds are obtained by synthesis processes which are inexpensive to be implemented. Furthermore, as it shall be best explained more thoroughly herein below, in the description section relating to the process and the plant, the novel compounds of the invention have a high efficiency in absorbing in liquid phase carbon dioxide and in the subsequent release without having the drawbacks of the conventional absorbers (for example, amines), such as a high volatility (resulting in environmental pollution), the strong basicity (resulting in a high corrosion of the plant) and their cost. In fact, due to the action of their low volatility, the compounds of the invention have thus a reduced environmental impact.

The object set forth above are also achieved by a process for the separation of carbon dioxide from a gaseous mixture, the process comprising the step of contacting said gaseous mixture containing carbon dioxide with an absorbent liquid comprising or composed of at least one compound, where such compound is a ionic liquid of the above-mentioned general formulae (I) and/or (II) and/or at least one ester of the above-mentioned formulae (III) and/or (V) under conditions such as to absorb the $CO_2$ in said absorbent liquid.

In the above-mentioned method, the compound of the invention, whether it is a ionic liquid of general formula (I) or (II) or an ester of general formula (III) or (V), is of per se a liquid which can be used in a pure state, or in mixture with one or more solvents (for example, a solution or emulsion).

In the case of mixture use, the use of mixtures between at least one ionic liquid according to the formula (I) or (II) and/or at least one ester according to the formula (III) or (V) and polar solvents, more preferably aprotic polar solvents is provided for.

The above-mentioned polar and aprotic polar solvents must have a sufficiently high boiling point, above 200° C., and they can be selected from the group comprising cyclic carbonates, propylene glycol, fatty alcohols with a number of carbon atoms above 8, and polyethylene glycol. Preferably, the polar compound is composed of propylene carbonate.

In another embodiment of the present invention, the use of the compounds of the invention in mixture with two immiscible solvents, an aprotic polar one and an apolar one is provided for. The aprotic polar solvent can be selected from the polar compounds indicated above. The apolar solvent must have a sufficiently high boiling point above 200° C. comparable to that of the above-mentioned polar solvents, and it can be selected from vegetal oils, carvone and linear hydrocarbons with a number of carbon atoms above 12. It is preferably vegetal oil.

The use of solvents such as those indicated above is optional, since, as noted above, it is possible to use the compounds of the invention in a pure state, whether they are ionic liquids or esters according to the invention, since such compounds are in the liquid state and already contain within the molecule both the amine polar portion binding CO2 (deriving from the amino acid) and the apolar portion, i.e., the C5-C19 alkyl chain. However, the use of solvents as those set forth above advantageously allows reducing the viscosity of the compounds of the invention, since the longer the alkyl chain of the compound of the invention is, for example, a ionic liquid, the higher is the viscosity thereof.

Furthermore, the use of polar solvents as those used above advantageously allows reducing the amount of heat that is lost by evaporation of the solvent in the CO2 releasing step with respect to the one that would be lost by using water as the solvent.

In the case that mixtures with polar compounds are used, the amount of compound of the invention in the mixture (for example, a solution) ranges between 30 and 60%, preferably between 40% and 60% by weight on the weight of the mixture, and it is selected so as to ensure viscosity characteristics to the resulting solution which are suitable to the sliding thereof in the implementation of the method according to the invention (in particular, a viscosity ranging between 4 cP and 30 cP, preferably between 5 cP and 10 cP). The optimal amount of the compound or solution thereof which is used in the process depends on the composition of the gaseous mixture, and in particular on the amount of carbon dioxide contained therein. Such amount can be readily determined by those skilled in the art based on their general knowledge.

The separation of carbon dioxide from the gaseous mixture is carried out with the method of the invention by absorption of carbon dioxide on at least one compound of the invention.

Preferably, the absorption process is carried out by contacting the gaseous mixture containing $CO_2$ with the at least one compound of the invention at a temperature ranging between 20° C. and 60° C., more preferably between 20° C. and 30° C., and at a pressure ranging between 1.5 and 10 bar.

The absorption of carbon dioxide occurs through the formation of carbamic acid on the primary or secondary amine of the amino acid and/or the amino-acyl group deriving from an amino acid or from the acyl residue of ectoin, according to the reaction generally set forth below with reference to a primary amine:

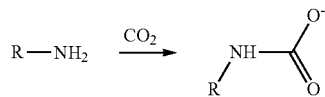

The molecule is stabilized by virtue of the formation of a hydrogen bridge with a second amino acid and/or with an amino-acyl group deriving from an amino acid or with an acyl residue of ectoin. The pressure typically promotes the absorption.

According to a preferred embodiment of the invention, the $CO_2$ separation (absorption) process is followed by a $CO_2$ releasing step in which the absorbent liquid containing $CO_2$ is treated under conditions such as to allow the desorption of $CO_2$, thereby obtaining a gaseous phase containing $CO_2$ and a regenerated absorbent liquid.

By the term "regenerated absorbent liquid" is meant the liquid containing at least one compound of the invention obtained at the end of the regeneration step, which is essentially free of $CO_2$ or has a reduced content of $CO_2$ (below 0.1%).

Advantageously, the $CO_2$ releasing and regeneration step of the absorbent liquid containing $CO_2$ can provide for the heating of the above-mentioned absorbent liquid containing $CO_2$ at a temperature ranging between 70° C. and 130° C., more preferably between 70° C. and 80° C., and the maintenance of such temperature for the time necessary to allow the release of carbon dioxide and consequently the regeneration of the absorbent liquid.

The suitable temperature and times for the release/regeneration step can easily be determined by those skilled in the art as a function, for example, of the composition of the absorbent liquid and the amount of $CO_2$, the latter being able to be monitored also continuously with suitable analysis methods which are per se conventional.

In particular, as it has already been inferred above, all the reference compounds, whether they are ionic liquids or esters, comprise, on one hand, an amino acid component (salified or not) or an ectoin component, which ensures the $CO_2$ absorption according to the mechanism illustrated above and, on the other hand, a component of medium-long C5-C19 alkyl chain, in particular C12-C19. The latter structural component of the molecules of the invention advantageously promotes the carbon dioxide releasing step in a manner comparable to the one which can be obtained by using a separated apolar solvent. At the same time, the combination of the above-mentioned two structural components confers to the compounds of the invention both suitable solubility characteristics in polar solvents optionally used therewith, and a sufficiently high boiling point, thereby avoiding the drawbacks of the prior art mentioned above, deriving from the use of apolar solvents for the CO2 releasing step.

A further advantage of the compounds of the invention is their higher biodegradability, since they are, in fact, obtained from materials of natural origin.

Advantageously, the method according to the present invention also provides for an increase in efficiency of the desorption step with respect to those already known. Stated in terms of $CO_2$ releasing speed, the method according to the present invention, allows not only more quickly releasing the carbon dioxide previously absorbed, but also obtaining a higher absolute value of regenerated absorbent liquid, when compared to an equal process carried out by using a known absorbent compound, not according to the invention.

Likewise advantageously, the method according to the present invention allows a decrease of the average thermal energy input for the same amount of absorber compounds to be regenerated with respect to systems containing ionic liquids or salts of amino acids similar to those provided for by the present invention, but completely deprived of C5-C19 medium-long alkyl chains. Stated in terms of temperature at which the $CO_2$ releasing process is completed, the method according to the present invention allows terminating the carbon dioxide releasing step at a lower temperature compared to the known compounds, not according to the invention.

Furthermore, it shall be stated, the compounds according to the present invention are amphiphilic, i.e., they have a polar head and a hydrophobic tail. Consequently, in the case that they are used in mixture with other types of solvents, such as co-polar solvents, or in an emulsion formed by two immiscible solvents, such as, for example propylene carbonate plus more a vegetal oil, they would thus tend to spontaneously arrange in micelles, with the amine group facing the polar one. Therefore, in these particular embodiments, the reaction with carbon dioxide is promoted, since the gas is more soluble in the polar phase, thus it more easily reacts with the hydrophilic head of the amphiphilic molecule. Also the stabilization of carbamate with a hydrogen bond is promoted by the orderly arrangement of the molecules in the micelles; in other words, such arrangement is optimal for the absorption of $CO_2$, since the carbamate ion charge of a molecule is compensated by the counterion ammonium of the neighbor molecule.

The above-mentioned objects are also achieved by a plant for the separation of $CO_2$ from a gaseous mixture and subsequent release of $CO_2$, comprising an absorption section comprising means for feeding a gaseous stream containing $CO_2$, means for feeding a stream of absorbent liquid preferably in countercurrent with respect to said gaseous stream containing $CO_2$, and means for the exit of a gaseous stream deprived of $CO_2$, a desorption (release of CO2) and regeneration section in fluid communication with said absorption section, said desorption and regeneration section comprising output means of a gaseous stream containing $CO_2$ and output means of a liquid stream of regenerated absorbent liquid, wherein each of said absorption section and said desorption and regeneration section comprise a sequence of first liquid/gas exchange areas preferably filled with a bed of inert material alternated with a sequence of second absorbent liquid collection areas and a plurality of interspaces arranged externally and adjacent to corresponding first liquid/gas exchange areas, each of said interspaces putting in fluid communication a second collection area with a successive first exchange area, so as to transfer said absorbent liquid from a second collection area to first exchange area successive thereto, a jacket outside said absorption section and a jacket outside said desorption and regeneration section, each being run along by thermal exchange fluid to carry out a thermal exchange between the absorbent liquid running along said interspaces and said thermal exchange fluid.

Preferably, each interspace has an outer length with a descending path followed by an inner length with an ascending path. Furthermore, the absorption section and the desorption section with their corresponding outer jackets can be arranged in succession in a single column, or preferably in two distinct columns in fluid communication to one another.

The provision of outer interspaces adjacent to the liquid-gas exchange areas for the liquid absorbent path from the collection areas and to the successive liquid/gas exchange areas, together with an outer jacket run along by a thermal exchange fluid to carry out a thermal exchange between the absorbent liquid running through said interspaces and said thermal exchange fluid advantageously allows keeping the absorbent liquid in the optimal temperature conditions for the inlet and the absorption or desorption on the entire volume of the first liquid/gas exchange areas.

In fact, it shall be noted that the CO2 absorption step is exothermic, while the CO2 absorption is endothermic. Therefore, the absorbent liquid is subjected to a thermal excursion both during the absorption step (temperature increase) and in the desorption step (temperature decrease), which leads it to reach temperatures at which the absorption efficiency and/or the desorption efficiency is not optimal, or it is sensibly reduced.

Instead, with the above-mentioned characteristics of the plant according to this embodiment of the invention, the absorbent liquid can be suitably cooled during the passage between successive first liquid/gas exchange areas of the absorption section by the thermal exchange fluid running through the outer jacket to the absorption section and, similarly, it can be suitably heated during the passage between successive first liquid/gas exchange areas of the desorption section by the thermal exchange fluid running through the outer jacket to the desorption section.

In this manner, the absorbent liquid is inserted in each first liquid/gas exchange area of the absorption section and the desorption section in the optimal temperature conditions, while minimizing thermal excursions between the central part of said first areas, farther from the outer jacket run through by the thermal exchange fluid, and the peripheral part of said first areas, nearer to the outer jacket run through by the thermal exchange fluid.

Further characteristics and advantages of the present invention will be apparent from the following description of a preferred embodiment, given by way of illustrative, non-limiting example, with reference to the appended drawings, in which:

FIG. 1 schematically shows a plant for the separation (absorption) of carbon dioxide from a gaseous mixture and subsequent release according to an embodiment of the method of the invention;

Figure 1:
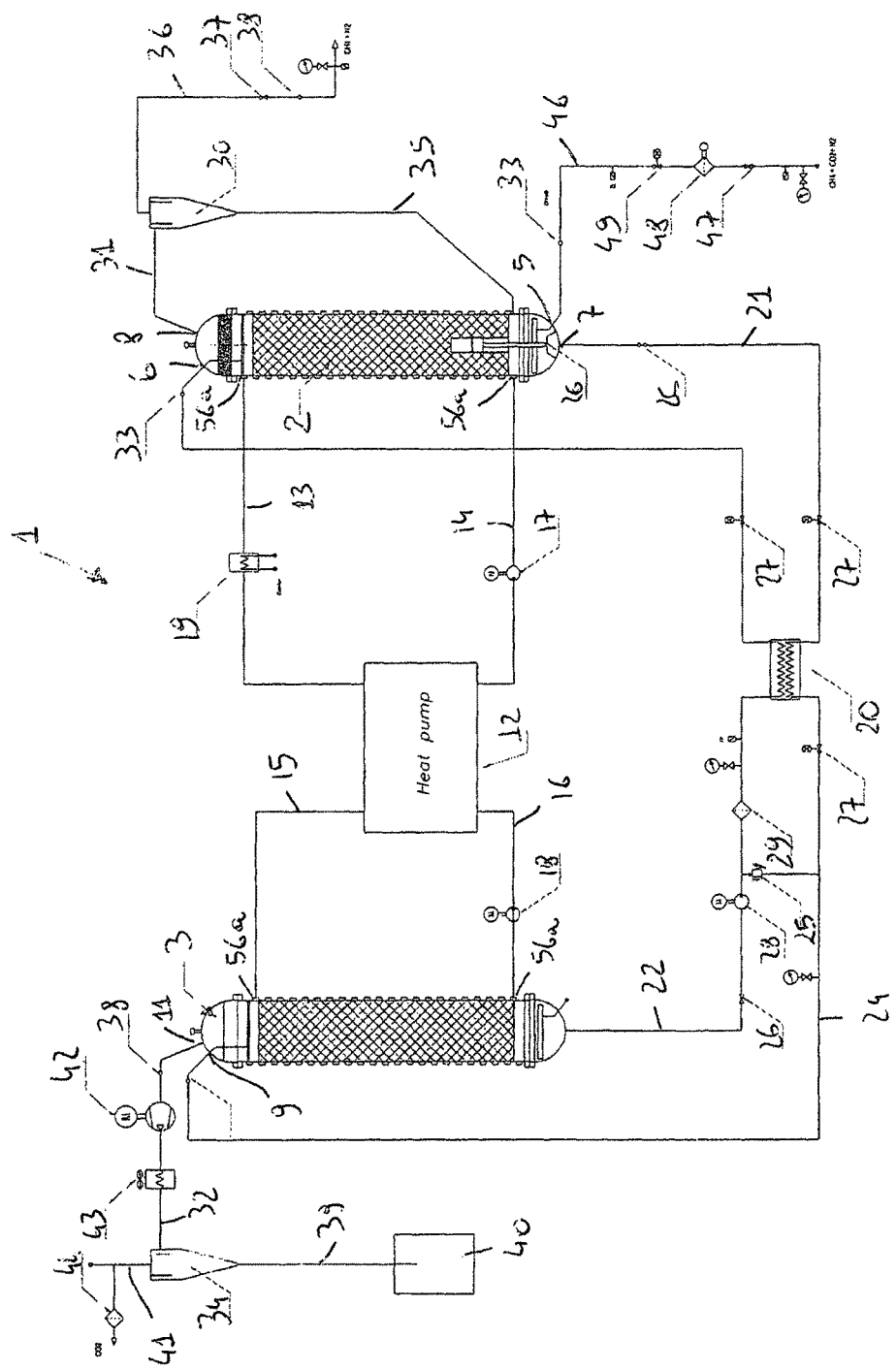
Figure 2:
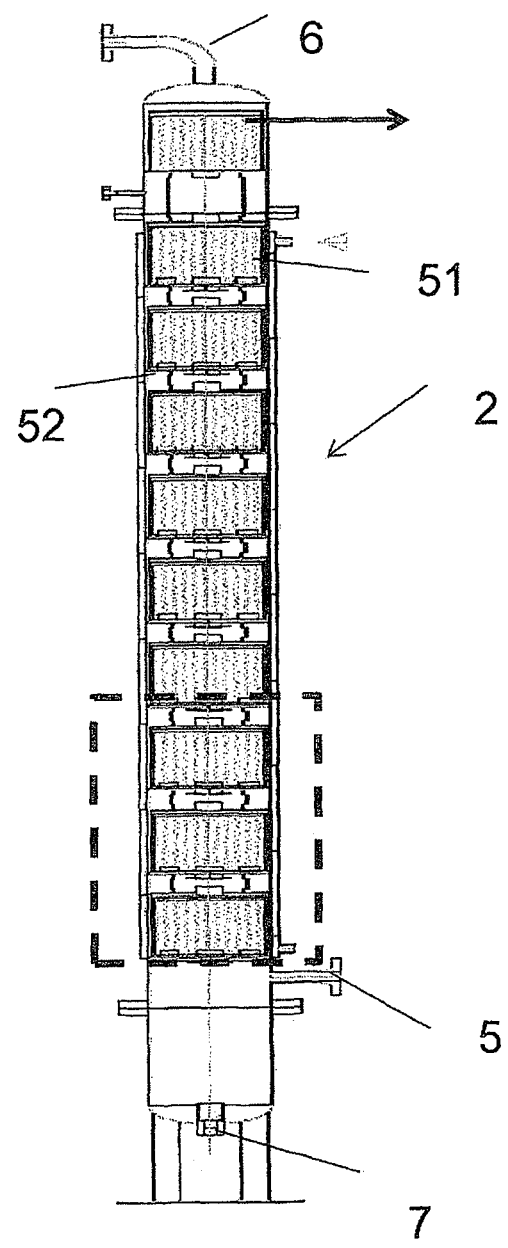
FIGS. 2 and 3 show a part and a detail, respectively, of the plant of FIG. 1.
Figure 3:
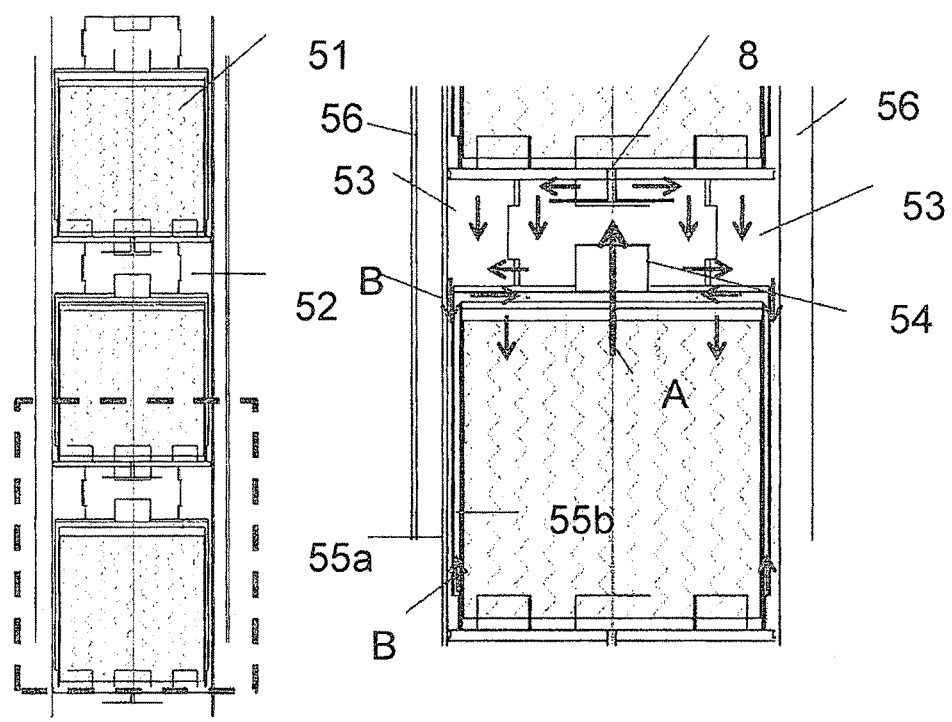

With reference to the FIGS. 1-3, a plant for the separation (absorption) of carbon dioxide from a gaseous mixture and subsequent release according to a first embodiment of the method of the invention is generally indicated with the reference 1.

The plant 1 comprises a first column 2 for the absorption of $CO_2$, and a second column 3 for the release of $CO_2$ and regeneration of the absorbent liquid, the above-mentioned columns being in a mutual fluid communication.

The absorption column 2 has a first opening 5 for the inlet of the gaseous mixture containing carbon dioxide to be separated, located at or in the proximity of the bottom, a second opening 6 for the inlet of the liquid-phase absorber for carbon dioxide located at or in the proximity of the top of the first column 2, a first outlet opening 7, located at or in the proximity of the bottom of the first column 2, for the passage of the absorbent liquid containing $CO_2$ in the second column 3, and a second outlet opening 8 located in the proximity of the top of the first column 2 for the exit of gases not absorbed by the absorbent liquid.

The gaseous mixture containing CO2 is fed to the first opening 5 of the absorption column 2 through the flow line 46 which can suitably contain an insulation ball valve 47, a filter 48, and an electrovalve 49.

The second column 3 for the release of CO2 and the regeneration of the solvent comprises an inlet opening 9 of the absorbent liquid containing CO2 coming from the first absorption column 2, the inlet opening 9 being arranged in the proximity of or at the top of the second column 3, a first outlet opening 10 for the regenerated absorbent liquid located in the proximity of or at the bottom of the second column 10, and a second opening 11 of a gaseous stream containing CO2 separated from the above-mentioned gaseous mixture.

More particularly, as illustrated in the FIGS. 2-3, the first column 2 is a sequence of first liquid/gas exchange areas 51 filled with a bed of inert material alternated with a sequence of second absorbent liquid collection areas 52 exiting the first thermal exchange areas 51. Each second collection area 52 has an absorbent liquid collection chamber 53 descending from the first upper thermal exchange area 51 immediately antecedent thereto, such absorbent liquid being inserted from said first area 51 into the chamber 53 of the second area 52 through a corresponding opening 8.

In each chamber 53 of a second collection area 52, the absorbent liquid is kept separated from the ascending gaseous stream containing CO2 running through the absorption column 2 in countercurrent with respect to the stream of absorbent liquid (arrow A). This is achieved by a plurality of tubes 54 connecting consecutive first exchange areas 51, each tube 54 passing through a second area 52 located between two consecutive first areas 51. Vice versa, in each first area 51, the ascending gaseous stream containing CO2 is in contact with the descending stream of absorbent liquid, thus carrying out a liquid/gas exchange which involves the absorption of CO2 in the absorbent liquid.

The absorption column 2 further comprises a plurality of interspaces 55 arranged externally and adjacent to corresponding first liquid/gas exchange areas 51. Each of such interspaces 55 put a second collection area 52, and precisely a collection chamber 53 of such second area 52 in fluid communication with the inlet of the successive first exchange area 51, so as to transfer said absorbent liquid from a second collection area to a first exchange area successive thereto.

In particular, each interspace 55 has an outer length 55a with a descending path followed by an inner length 55a with an ascending path, so as to make the absorbent liquid run a coil-shaped path before it is introduced in a successive first liquid/gas exchange area 51 (arrows B).

Advantageously, the first column 2 is also provided with an jacket 56 external to the first absorption areas 51, the second collection areas 52, and the interspaces 55 of the absorption section 2 intended to be run through by a cooling fluid, so as to carry out a thermal exchange with the absorbent liquid running through said interspaces 55. In the present embodiment, the outer jacket is arranged vertically substantially along the entire length of the absorption column 2, and it can be divided into sections 56a in fluid communication with one another.

With such solution, the absorbent liquid is inserted in each first liquid/gas exchange area 51 of the absorption column 2 under the optimal temperature conditions, of while minimizing thermal excursions between the central part of said first areas 51, farther from the outer jacket 56 run through by the cooling fluid, and the peripheral part of said first areas 51, nearer to the outer jacket 56 run through by the cooling fluid.

The same solution can be advantageously adopted also in the desorption column 3, which can therefore have a plurality of regeneration areas 51, alternated with absorbent liquid collection areas 52, an interspace path 55 for the absorbent liquid to be transferred from a regeneration area 51 to a successive regeneration area 51, and an outer jacket to the areas 51,52 and the interspaces 55 to carry out an indirect thermal exchange, with an outer jacket which this time is run through by a heated fluid.

The possibility to limit the thermal excursion in the columns 2 and 3 associated to the absorption and release processes, respectively, allows keeping in the two columns the absorbent liquid at a temperature preferably in a range between 70-80° C. for the regeneration column 3 and between 20-30° C. for the absorption column 2.

The plant 1 further comprises a heat pump 12 in fluid communication with the upper sections 56a and the lower section 56a of the jacket 56 of the absorption column 2 through the flow lines (tubing) 13 and 14, respectively, and in fluid communication with the upper sections 56a and the lower section 56a of the jacket 56 of the regeneration column 3 through the flow lines (tubing) 15 and 16, respectively.

The heat pump 12 advantageously allows subtracting heat from the thermal exchange fluid exiting the lower section 56a of the absorption column 2—which reaches the pump 12 through the flow line 14 with the aid of a pump 17 in such line 14—and transferring the heat extracted from the thermal exchange fluid exiting the lower section 56a of the regeneration column 3—which reaches the pump 12 via the flow line 16 with the aid of a pump 18 in such line 16. The thermal exchange fluid heated by the heat pump 12 can then be inserted back in the upper section 56 of the outer jacket 56 of the regeneration column 3 through the flow line 15, while the thermal exchange fluid cooled by the heat pump 12 can then be inserted back in the upper section 56a of the outer jacket 56 of the absorption column 2 via the flow line 13, along which it can be subjected to a further cooling by a heat exchanged 19 arranged in-line.

In this manner, the energy input from the outside is reduced.

The plant 1 further comprises a further heat exchanger 20 in fluid communication with the columns 2,3, which receives in separated flows, through corresponding flow lines 21 and 22, the absorbent liquid containing absorbed CO2 exiting the outlet opening 7 of the absorption column 2 and the regenerated absorbent liquid exiting the outlet opening 10 of the regeneration column 3. In the heat exchanger 20, such separated flows are subjected to a suitable indirect thermal exchange, then they are sent to the columns 2,3, in particular, the regenerated absorbent liquid to the inlet opening 6 of the absorption column 2 through the flow line 23, for a successive absorption cycle, and the absorbent liquid containing absorbed CO2 to the inlet opening 9 of the regeneration column 2 through the flow line 24 for a successive subsequent cycle of CO2 release and regeneration of the absorbent liquid.

Suitable means for the adjustment and control of the flows can be arranged along the flow lines 21,22,23 and 24, which, in particular, a maximum pressure valve 25, an insulation ball valve 26 in the flow line 22, check valves 33 in the flow lines 23 and 24, and electrovalves 27 in the flow lines 21, 23 and 24. Furthermore, a pressurizing pump 28 and a filter 29 can be provided in the flow line 22.

The plant 1 further comprises a first cyclone 30 in fluid communication with the outlet opening 8 of the gaseous stream deprived of CO2 from the absorption column 2 through the flow line 31, and a second cyclone 34 in fluid communication with the outlet opening 11 of the gaseous stream containing CO2 separated from the release and regeneration column 3 through the flow line 32.

The first cyclone 30 allows separating possible liquid dragged by the gaseous stream deprived of CO2 exiting the absorption column 2. The liquid separated in the first cyclone 30 is recycled to the absorption column 2 through the flow line 35, while the gaseous stream deprived of the liquid exiting the first cyclone 30 is recovered through the flow line 36.

Advantageously, a suitable insulation ball valve 37 and a suitable check valve 38 can be inserted in the flow line 36.

The second cyclone 30 allows separating the possible liquid carried by the gaseous stream containing CO2 separated from the releasing and regeneration column 3. The liquid separated in the second cyclone 34 is suitably recovered in the reservoir 40 through the flow line 39, while the gaseous stream deprived of the liquid exiting the second cyclone 34 is recovered via the flow line 41.

Advantageously, a suitable check valve 38, a vacuum pump 42, and a heat exchanger 43 (gas cooler) can be inserted in the flow line 32, while a suitable filter 44 can be inserted in the flow line 41.

Further characteristics and advantages of the present invention will be apparent from the following examples, of given by way of illustrative, non-limiting example.

EXAMPLE 1

0.2 moles of glycine salified with choline hexyl-ester (a compound according to the invention) is dissolved in 100 ml of a solution of propylene carbonate containing 10% in volume vegetal oil. The solution is stirred for 20 minutes and sonicated during 5 minutes until a stable emulsion is obtained.

A comparison emulsion containing the same mixture of solvents and glycine salified with choline (a compound not according to the invention) is then similarly prepared.

Next, the emulsion according to the invention is put in an absorption column filled with Raschig rings to increase the gas-liquid contact surface. Next, a gas composed of 10% $CO_2$ in nitrogen with a flow of 45 L/h is made to flow. During this step, the temperature measured with the aid of a thermocouple passes from the initial 20° C. to 32° C. The absorption is stopped when the $CO_2$ detector arranged at the column outlet opening measures, inside the exiting gaseous mixture, a mass % amount of $CO_2$ above 5%. The absorption step takes 30 minutes on average (Such step is highlighted in the graph of FIG. 6 by a double arrow). The releasing step is monitored during a temperature scan of the column, starting from 30° C. up to 130° C., with a scanning rate of 2° C./min, and it is subsequently kept at 130° C. during 50 minutes.

The same type of procedure is carried out in order to test a comparison emulsion containing glycine salified with choline. The results of the comparison test were compared to the one previously carried out on the emulsion containing glycine salified with choline, a compound according to the invention.

Figure 4:
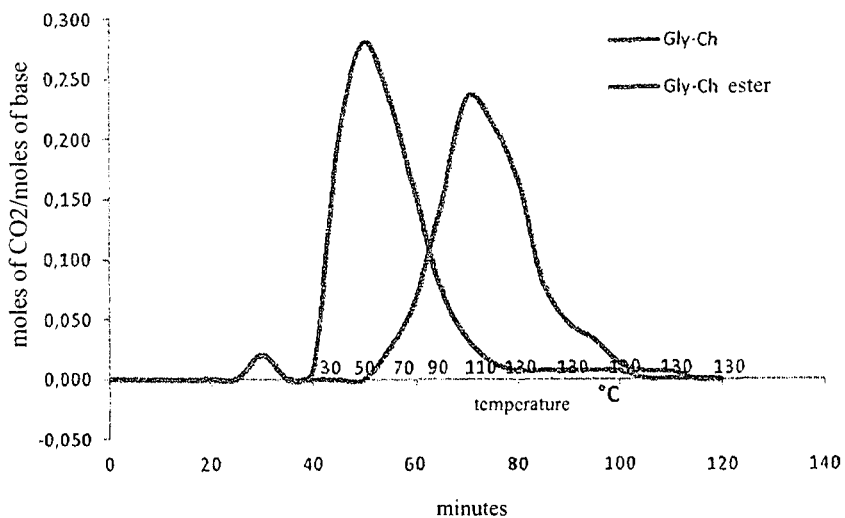
FIG. 4 shows a graph illustrating the $CO_2$ concentration change in the absorbent liquid in an implementation example of the process according to the invention, compared to the $CO_2$ change of a compound not according to the invention.

With reference to FIG. 4, the release temperature of a comparison emulsion is sensibly higher compared to that of the emulsion containing glycine salt with choline hexanoate. Again, the curve slope, in the decreasing phase, indicates a higher difficulty of the Gly-Ch molecule in releasing $CO_2$ compared to the ester.

EXAMPLE 2

The procedure of the example 1 was repeated replacing the ionic liquid of such example with the following glycerol ester with glycine and hexanoic acid.

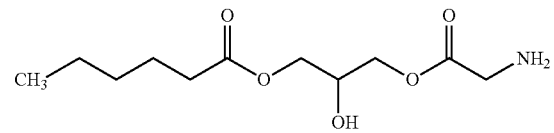 [SMILES: CCCCCC(=O)OCC(O)COC(=O)CN]

Results completely comparable to those obtained in example 1 were obtained by the use of the glycine salt with choline esterified with hexanoic acid. In particular, the ester tested in this example showed reactivity to $CO_2$ essentially identical to that of the ionic liquid of the example 1, having in fact amino acids (in particular, glycine) with the same amine group.

EXAMPLE 3

The procedure of the example 1 was repeated in order to obtain and test two different 3M propylene carbonate solutions of hexyl glycinate (a compound according to the invention) and potassium glycinate (a compound non according to the invention), respectively.

Figure 5:
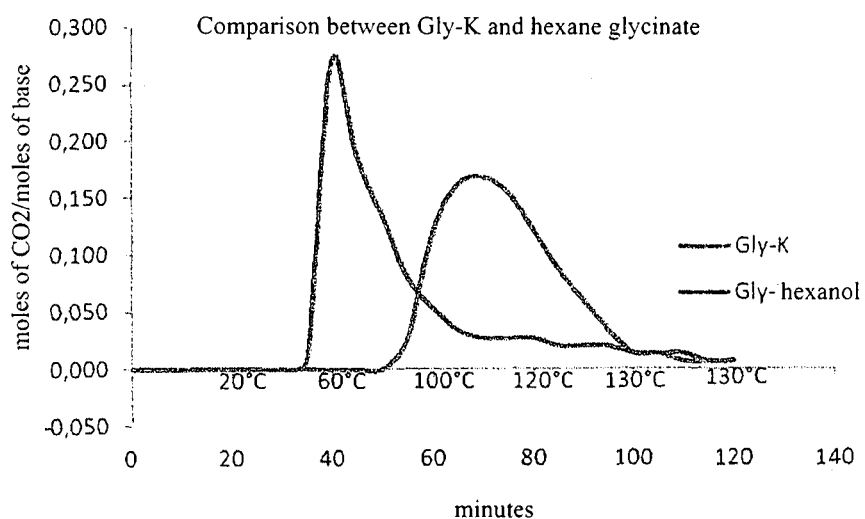
FIG. 5 shows a graph illustrating the $CO_2$ concentration change in the absorbent liquid in another implementation example of the process according to the invention, compared to the $CO_2$ change of a compound not according to the invention.

With reference to FIG. 5, results completely comparable to those obtained in example 1 were obtained. In particular, the absorption shows about the same trend: from the graph, it is possible to indicate a flat portion during the first 30 minutes, which precisely correspond to the absorption step, where the column temperature is kept at a value of 20° C. Furthermore, the carbon dioxide release occurs for the ester at a considerably lower temperature compared to that for the potassium salt: the release starts at 55° C., and at approximately 80° C. the amount of released $CO_2$ is more than 80%. Instead, for the salt the release occurs at a temperature above 120° C.

EXAMPLE 4

The procedure of the example 1 was repeated in order to obtain a 3M propylene carbonate solution of hexyl glycinate.

Such solution is arranged in an absorption column filled with Raschig rings to increase the gas-liquid contact surface. Next, a gas composed of 10% $CO_2$ in nitrogen with a flow of 45 L/h is made to flow. During this step, the temperature measured with the aid of a thermocouple passes from the initial 20° C. to final 32° C. The absorption is stopped when the $CO_2$ detector arranged at the column outlet opening measures, inside the exiting gaseous mixture, a mass % amount of $CO_2$ above 5%. The absorption step takes 30 minutes on average. The successive releasing step is carried out while keeping the column at a constant temperature of 70° C. during 60 minutes. The comparison solution is an aqueous solution of 30% (5M) ethanolamine (MEA).

Figure 6:
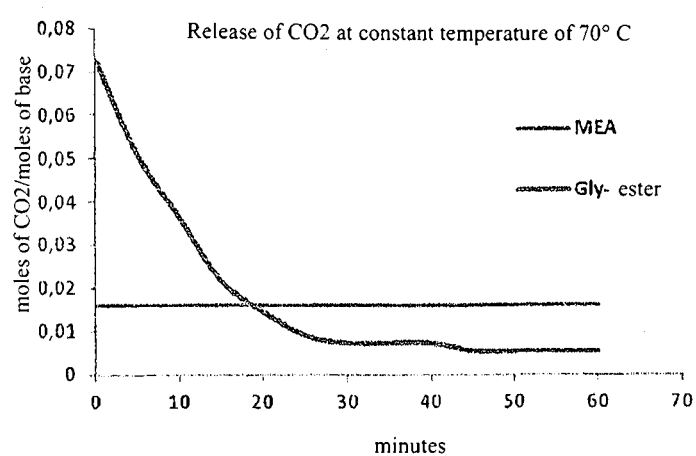
FIG. 6 shows a graph illustrating the $CO_2$ concentration change in the absorbent liquid in a further implementation example of the process according to the invention, compared to the $CO_2$ change of a compound not according to the invention.

With reference to FIG. 6, while having the same efficiency in the absorption step, when the solutions are subjected to a temperature of 70° C. in a nitrogen flow, the releasing rate is definitely in favor of the ester, which releases more than 65% $CO_2$ in the first 20 minutes; instead, the control solution containing MEA has a release quantitatively much lower and constant throughout the duration of the experiment (with a considerable loss of vapor).

The invention claimed is:

1. A compound for the absorption of carbon dioxide in the form of ionic liquids having the following general formula (I) or (II):

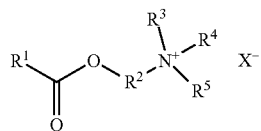

(I)

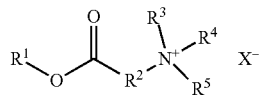

(II)

wherein R3, R4, R5 are each independently H, a C1-C6 alkyl group or an aromatic group, R2 is a C1-C6 alkyl group, R1 is a C5-C19 alkyl group, and X⁻ is a carboxylate anion of a natural or artificial amino acid, or in the form of glycerol esters having the general formula (III):

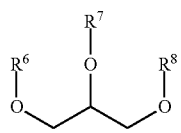

(III)

wherein the groups R6, R7 and R8 are selected from H, an acyl group of formula R⁹—C(=OR)— where R9 is a C5-C19 alkyl group, an amino-acyl group deriving from a natural or artificial amino acid or an acyl residue of ectoin of formula (IV),

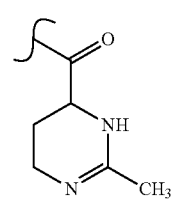

(IV)

and wherein at least one of the groups R6, R7, R8 is an acyl group of formula R⁹—C(=OR)— and at least one of the groups R6, R7, R8 is an amino-acyl group deriving from a natural or artificial amino acid or an acyl residue of ectoin of formula (IV), or in the form of esters, having the general formula (V)

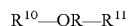

(V)

wherein R10 is a C5-C19 alkyl group and R11 is an amino-acyl group deriving from a natural or artificial amino acid or an acyl residue of ectoin of formula (IV).

2. The compound for the absorption of carbon dioxide according to claim 1, which is selected from the group consisting of a glycine salt with choline hexanoate, an ester between glycine and hexanoic alcohol (hexyl glycinate) and a glycerol ester with glycine and hexanoic acid having the following formula:

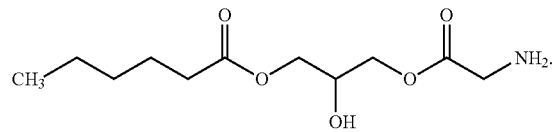 [SMILES: CCCCCC(=O)OCC(O)COC(=O)CN]

3. A process for the separation of carbon dioxide from a gaseous mixture, the process comprising the step of contacting said gaseous mixture containing carbon dioxide with at least one absorbent liquid comprising a compound, wherein said compound is an ionic liquid of the following general formula (I) or (II):

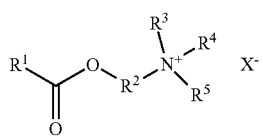

(I)

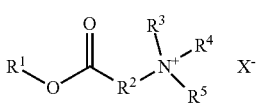

(II)

wherein R3, R4, R5 are each independently H, a C1-C6 alkyl group or an aromatic group, R2 is a C1-C6 alkyl group, R1 is a C5-C19 alkyl group, and $X^{31}$ 0 is a carboxylate anion of a natural or artificial amino acid, and/or at least one glycerol ester having the general formula (III):

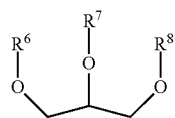

(III)

wherein the groups R6, R7 and R8 are selected from H, an acyl group of formula $R^9$—C(=OR)— where R9 is a C5-C19 alkyl group, an amino-acyl group deriving from a natural or artificial amino acid or an acyl residue of ectoin of formula (IV),

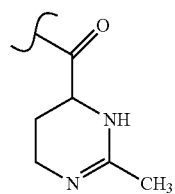

(IV)

and wherein at least one of the groups R6, R7, R8 is an acyl group of formula $R^9$—C(=OR)— and at least one of the groups R6, R7, R8 is an amino-acyl group deriving from a natural or artificial amino acid or an acyl residue of ectoin of formula (IV), or in the form of an ester, having the general formula (V):

$$R^{10}-OR-R^{11} \qquad (V)$$

wherein R10 is a C5-C19 alkyl group and R11 is an amino-acyl group deriving from a natural or artificial amino acid or an acyl residue of ectoin of formula (IV) under conditions such as to absorb $CO_2$ in said absorbent liquid.

4. The process according to claim 3, wherein the absorbent liquid is composed of said compound or a mixture comprising said compound.

5. The process according to claim 4, wherein said absorbent liquid is composed of:
a mixture between at least one ionic liquid according to the formula (I) or (II), and/or
at least one ester according to the formula (III) or (V), and a polar solvent.

6. The process according to claim 4, wherein said absorbent liquid is composed of:
a mixture between at least one ionic liquid according to the formula (I) or (II), and/or
at least one ester according to the formula (III) or (V), and two immiscible solvents, wherein the immiscible solvents are an aprotic polar solvent and an apolar solvent.

7. The process according to claim 5, wherein said aprotic polar solvent has a boiling point above 200° C.

8. The process according to claim 6, wherein said aprotic polar solvent has a boiling point above 200° C.

9. The process according to claim 8, wherein said apolar solvent has a boiling point above 200° C.

10. The process according to claim 5, further comprising a releasing step of $CO_2$ in which the absorbent liquid containing $CO_2$ is treated under conditions to allow the desorption of $CO_2$, thereby obtaining a gaseous phase containing $CO_2$ and a regenerated absorbent liquid.

11. A plant for the separation of $CO_2$ from a gaseous mixture and subsequent release of $CO_2$, comprising a column having:

an absorption section (2) comprising means (5) for feeding a gaseous stream containing $CO_2$, means (6) for feeding a stream of absorbent liquid, and means (8) for the exit of a gaseous stream deprived of $CO_2$,
a desorption (release of $CO_2$) and regeneration section (3) in fluid communication with said absorption section (2), said desorption and regeneration section comprising output means (11) for a gaseous stream containing $CO_2$ and output means (10) for a liquid stream of regenerated absorbent liquid,
wherein said absorption section (2) and said desorption and regeneration section (3) each comprise a sequence of first areas (51) of liquid/gas exchange, alternated with a sequence of second areas (52) for the collection of absorbent liquid and a plurality of interspaces (55) arranged externally and adjacent to corresponding first liquid/gas exchange areas (51), each of said interspaces (55) putting in fluid communication a second collection area (52) with a successive first exchange area (51) so as to transfer said absorbent liquid from a second collection area (52) to a first exchange area (51) subsequent thereto,
a jacket (56) outside said absorption section (2) and a jacket (56) outside said desorption and regeneration section (3), each run through by a thermal exchange fluid to carry out a thermal exchange between the absorbent liquid running through said interspaces (55) and said thermal exchange fluid,
wherein each interspace (55) has an outer length (55a) with a descending path, followed by an inner length (55b) with an ascending path.

12. A process for the absorption of $CO_2$ and subsequent release by means of the plant according to claim 11, the process comprising the steps of:
feeding a gaseous stream containing $CO_2$ and a stream of absorbent liquid
contacting said gaseous stream containing $CO_2$ and said stream of absorbent liquid in said absorption section (2), obtaining a gaseous stream substantially deprived of $CO_2$ and a stream of absorbent liquid containing $CO_2$,
feeding said stream of absorbent liquid containing $CO_2$ in said desorption and regeneration section (3), obtaining a gaseous stream containing $CO_2$ and a flow of regenerated absorbent liquid.

13. The process according to claim 5, wherein the polar solvent is an aprotic polar solvent.

14. The process according to claim 7, wherein the aprotic polar solvent is selected from the group consisting of cyclic carbonates, propylene glycol, fatty alcohols with a number of carbon atoms higher than 8 and polyethylene glycol.

15. The process according to claim 8, wherein the aprotic polar solvent is selected from the group consisting of cyclic carbonates, propylene glycol, fatty alcohols with a number of carbon atoms higher than 8 and polyethylene glycol.

16. The process according to claim 9, wherein the apolar solvent is selected from the group consisting of vegetal oils, carvone and linear hydrocarbons with a number of carbon atoms above 12.

17. The plant according to claim 11, wherein the stream of absorbent liquid is in countercurrent with respect to said gaseous stream containing $CO_2$ in said absorption section (2).

18. The plant according to claim 11, wherein the first areas (51) of liquid/gas exchange are filled with a bed of inert material.

19. The process according to claim 12, wherein the stream of absorbent liquid is in countercurrent in said absorption section (2).

* * * * *